(12) United States Patent
Itoi et al.

(10) Patent No.: US 11,452,625 B2
(45) Date of Patent: Sep. 27, 2022

(54) STENT

(71) Applicants: Takao Itoi, Tokyo (JP); SB-KAWASUMI LABORATORIES, INC., Kanagawa (JP)

(72) Inventors: Takao Itoi, Tokyo (JP); Noriaki Shirahama, Oita (JP)

(73) Assignees: Takao Itoi, Tokyo (JP); SB-KAWASUMI LABORATORIES, INC., Kanagawa (JP)

( * ) Notice: Subject to any disclaimer, the term of this patent is extended or adjusted under 35 U.S.C. 154(b) by 0 days.

(21) Appl. No.: 17/041,540

(22) PCT Filed: Apr. 22, 2019

(86) PCT No.: PCT/JP2019/016931
§ 371 (c)(1),
(2) Date: Sep. 25, 2020

(87) PCT Pub. No.: WO2019/208467
PCT Pub. Date: Oct. 31, 2019

(65) Prior Publication Data
US 2021/0022893 A1 Jan. 28, 2021

(30) Foreign Application Priority Data

Apr. 27, 2018 (JP) .............................. JP2018-086854

(51) Int. Cl.
*A61F 2/86* (2013.01)
*A61F 2/82* (2013.01)
*A61F 2/04* (2013.01)

(52) U.S. Cl.
CPC .................. *A61F 2/86* (2013.01); *A61F 2/04* (2013.01); *A61F 2/82* (2013.01); *A61F 2002/041* (2013.01)

(58) Field of Classification Search
CPC ...... A61F 2/04; A61F 2/82; A61F 2/86; A61F 2/90; A61F 2/95; A61F 2002/041
See application file for complete search history.

(56) References Cited

U.S. PATENT DOCUMENTS 6,821,291 B2 * 11/2004 Bolea .................. A61F 2/90
606/108
2001/0004705 A1 6/2001 Douglas
(Continued)

FOREIGN PATENT DOCUMENTS

EP 2967821 A2 1/2016
JP 2003325673 A 11/2003
(Continued)

OTHER PUBLICATIONS

English Translation of JP 2008-000193 (disclosed in IDS dated Sep. 25, 2020) (Year: 2008).*
(Continued)

*Primary Examiner* — Dinah Baria
(74) *Attorney, Agent, or Firm* — Brundidge & Stanger, P.C.

(57) ABSTRACT

Provided is a stent which is not easily displaced from a dwell site in a biological lumen and which has an excellent ability to follow a biological lumen. This stent (bile duct stent 100) is to dwell inside a biological lumen (bile duct B) and is provided with a stent main body section (110) having a cylindrical shape. The stent main body section is configured to be capable of expanding and contracting in the radial direction that is approximately orthogonal to an axial direction, has a relatively large expanding force in one portion (center portion) corresponding to the predetermined position at the indwelling site in the biological lumen, and a relatively small expanding force at other portions (both end
(Continued)

portions) which have different positions in the axial direction from that of the one portion.

4 Claims, 4 Drawing Sheets

(56) References Cited

U.S. PATENT DOCUMENTS

| | | |
|---|---|---|
| 2004/0034403 A1 | 2/2004 | Schmitt |
| 2007/0179590 A1 | 8/2007 | Wengeng |
| 2013/0289697 A1* | 10/2013 | Baker ............... A61F 2/962 623/1.12 |
| 2014/0379092 A1 | 12/2014 | Anai |
| 2015/0282922 A1 | 10/2015 | Hingston |
| 2018/0028337 A1 | 2/2018 | Toyokawa et al. |

FOREIGN PATENT DOCUMENTS

| | | |
|---|---|---|
| JP | 2006506209 A | 2/2006 |
| JP | 2008-000193 A | 1/2008 |
| JP | 4651943 B2 | 3/2011 |
| JP | 2017-513582 A | 6/2017 |
| WO | 2004-045450 A2 | 6/2004 |
| WO | 2013/115141 A1 | 8/2013 |
| WO | 2014153267 A2 | 9/2014 |
| WO | 2016/129551 A1 | 8/2016 |

OTHER PUBLICATIONS

International Search Report from International Application No. PCT/JP2019/016931 dated Jun. 18, 2019.
Extended European Search report dated Oct. 6, 2021.

* cited by examiner

STENT

TECHNICAL FIELD

The present invention relates to a stent to be placed in a living body lumen.

BACKGROUND ART

Conventionally, there has been a known stent that is placed in a stenosis site or an occluded site generated in a living body lumen such as blood vessel, esophagus, bile duct, trachea, and urinary duct, and increases a diameter of a lesion site to maintain an opening state of the living body lumen (for example, see Patent Document 1).

PRIOR ART DOCUMENT

Patent Document

Patent Document 1: Japanese Patent Publication No. 4651943

SUMMARY OF THE INVENTION

Technical Problem

However, in the cases of Patent Document 1 and the like, a stent can easily follow a living body lumen by improving flexibility of the stent, but if an expanding force of the stent is small, there is a problem that the stent tends to be displaced from an indwelling site in the living body lumen. On the other hand, if the expanding force of the stent is increased, adhesiveness of the stent to the living body lumen is improved, so that the stent is hardly displaced, but accordingly an axial force also increases, and the stent hardly follows the living body lumen. In addition, when the stent is placed again, the stent may be difficult to remove from the living body lumen. To improve adhesiveness to the living body lumen, it is not sufficient to simply increase the expanding force of the stent.

An object of the present invention is to provide a stent that is hardly displaced from an indwelling site in a living body lumen and has good followability to the living body lumen.

Solution to Problem

The stent according to the present invention is a stent that is placed in a living body lumen, the stent including a stent main body section in a cylindrical shape, wherein the stent main body section is formed expandably and contractibly in a radial direction substantially orthogonal to an axial direction, and has a portion that corresponds to a predetermined position on an indwelling site in the living body lumen and exerts a relatively large expanding force, and a different portion that is different in axial position from the portion and exerts a relatively small expanding force.

Advantageous Effect of the Invention

According to the present invention, the stent is hardly displaced from the indwelling site in the living body lumen, and followability of the stent to the living body lumen can be improved.

DESCRIPTION OF THE EMBODIMENT

Hereinafter, the embodiment of the present invention will be explained in detail with reference to the figures. In this embodiment, as an example of the present invention, a bile duct stent 100 will be explained, which is placed in a bile duct B and used in order to treat occlusion (stenosis) by widening a lesion site of the bile duct B (e.g. occluded site or stenosis site of the bile duct B) (see FIG. 4A) outward in a radial direction.

Figure 1:
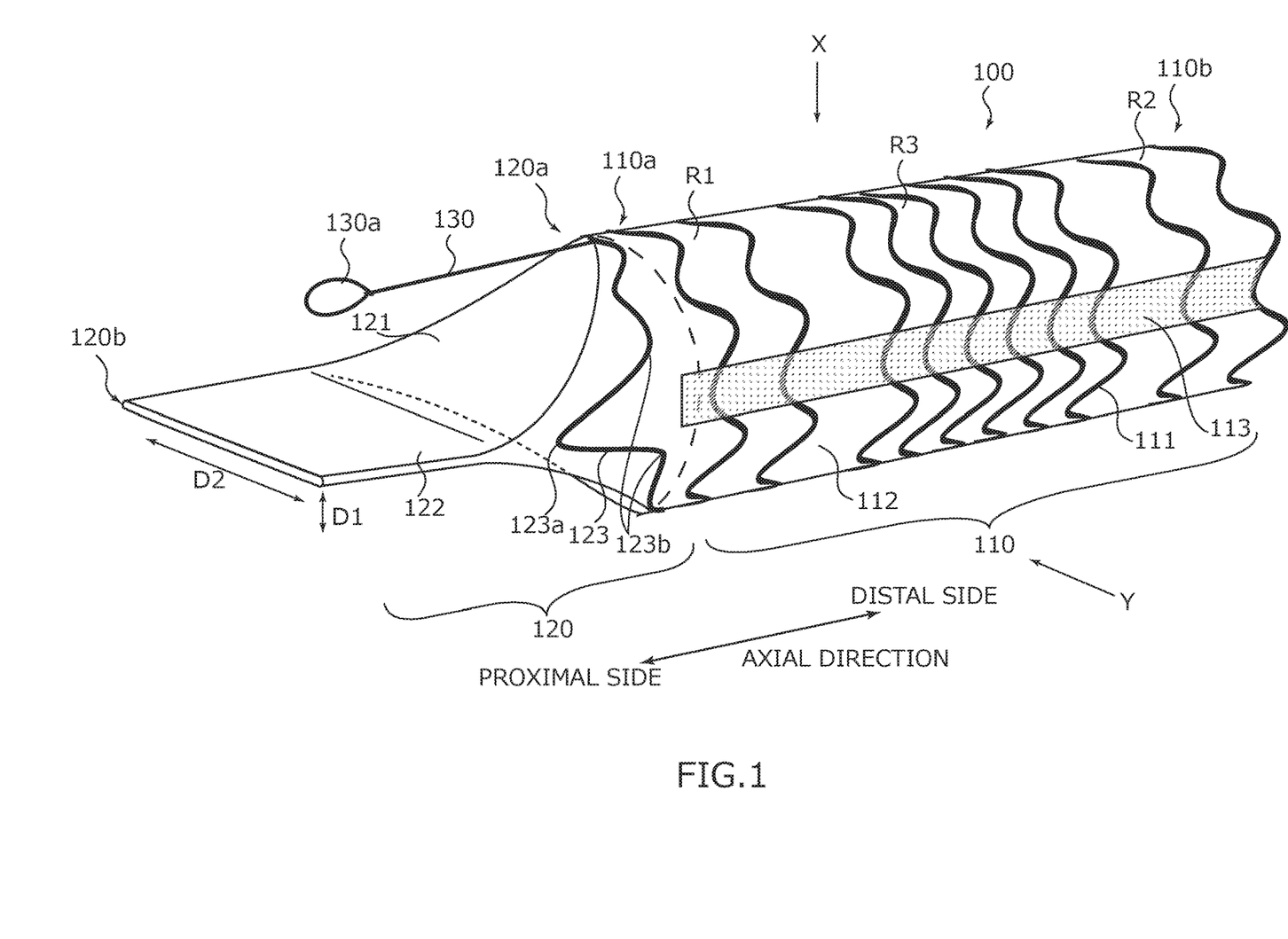
FIG. 1 is an external perspective view illustrating a configuration of a bile duct stent according to an embodiment.
Figure 2A:
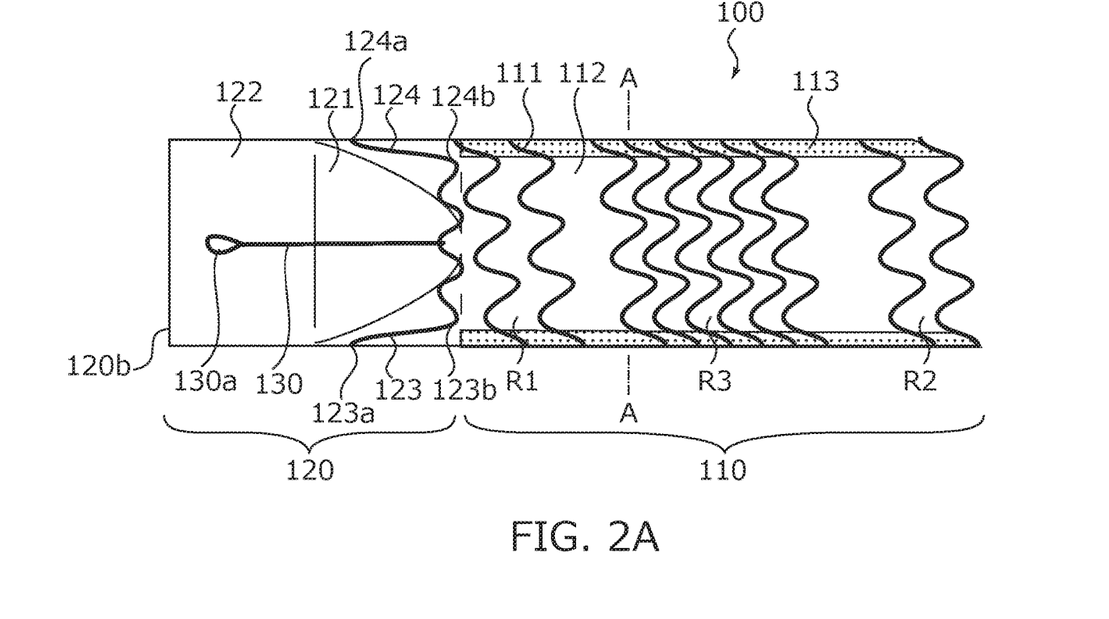
FIG. 2A is a plan view illustrating the configuration of the bile duct stent.
Figure 2B:
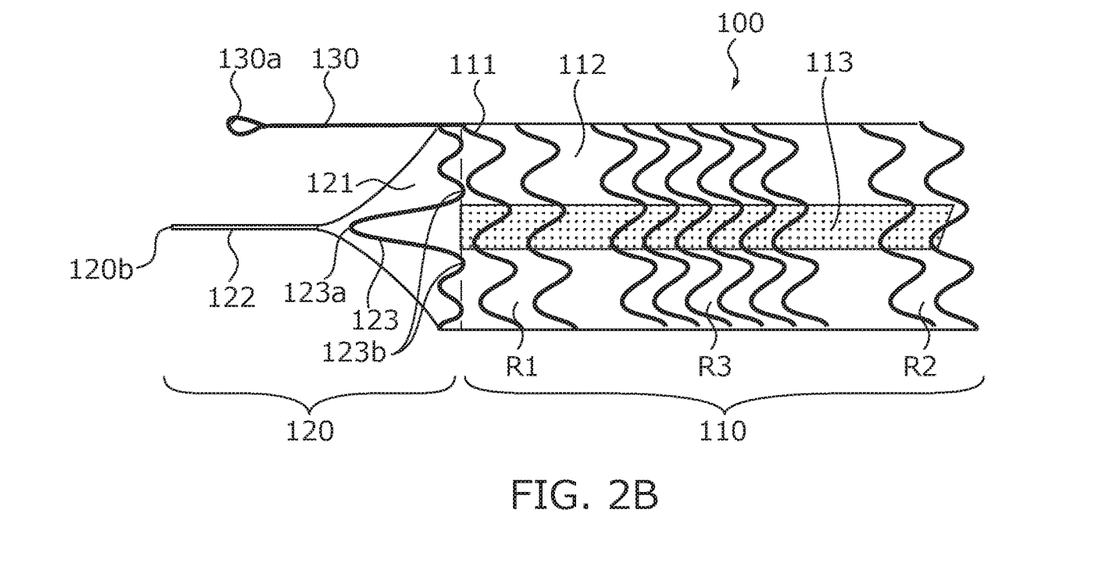
FIG. 2B is a side view illustrating the configuration of the bile duct stent.
Figure 3:
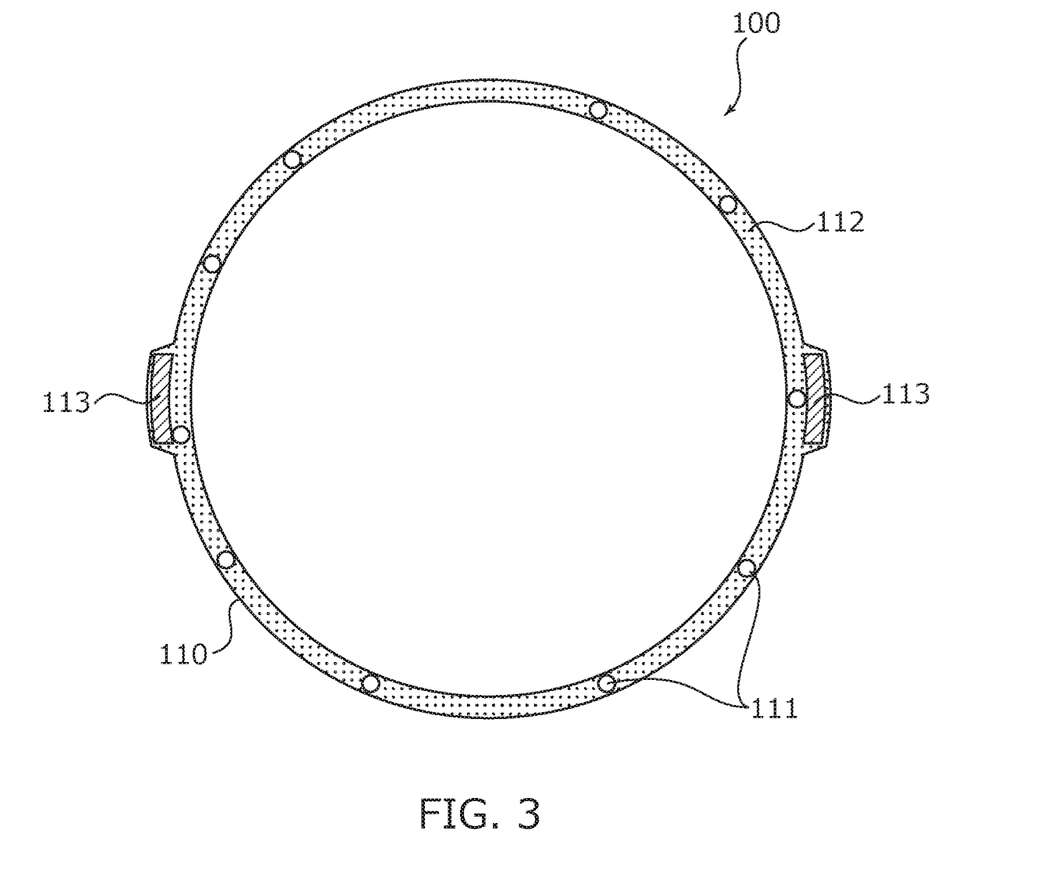
FIG. 3 is a sectional view illustrating a stent main body section.

FIG. 1 is a perspective view illustrating the bile duct stent 100, FIG. 2A is a plan view illustrating the bile duct stent 100 viewed from an X direction in FIG. 1, and FIG. 2B is a side view illustrating the bile duct stent 100 viewed from a Y direction in FIG. 1. In addition, FIG. 3 is a sectional view illustrating a stent main body section 110 taken along line A-A in FIG. 2A. As illustrated in FIG. 1 to FIG. 3, the bile duct stent 100 includes the stent main body section 110, a valve section 120, and a removal assistant 130.

The stent main body section 110 has a cylindrical shape that demarcates a flow path for bile. In the stent main body section 110, one end portion 110a positioned on a left front side in FIG. 1 is referred to as "first end portion 110a", and a different end portion 110b positioned on a right back side in FIG. 1 is referred to as "second end portion 110b". The bile duct stent 100 is placed in the bile duct B such that the first end portion 110a is positioned on a downstream side and the second end portion 110b is positioned on an upstream side in a bile flow direction (see FIG. 4, and the like).

The stent main body section 110 has a skeleton portion 111, a membrane portion 112, and a stretch restriction portion 113.

The skeleton portion 111 is a stiffening member that holds the membrane portion 112 in a predetermined expansion state. For example, the skeleton portion 111 is a self-expandable stent skeleton formed into a cylindrical shape by spirally winding a metal wire rod while the metal wire rod is bended such that crest portions and trough portions are alternately formed in the axial direction.

The skeleton portion 111 is configured to be self-expandable in the radial direction substantially orthogonal to the axial direction, from a contraction state where the skeleton portion 111 contracts inward to an expansion state where the skeleton portion 111 expands outward to demarcate a cylindrical flow path. For example, when the skeleton portion 111 is pulled in the axial direction, the skeleton portion 111 contracts inward in the radial direction and stretches in the axial direction. On the other hand, when the skeleton portion 111 is released from the contraction state, the skeleton portion 111 shortens in the axial direction while expanding outward in the radial direction by a self-expanding force.

In the bile duct stent 100, an outer face of the stent presses an inner face of the bile duct B by the self-expanding force of the skeleton portion 111, and in this state, the skeleton portion 111 can be deformed according to an external force applied from the outer face side of the stent. That means, the skeleton portion 111 is stretchable in the axial direction and has a cylindrical shape capable of expanding and contracting in the radial direction substantially orthogonal to the axial direction.

Examples of a material of the metal wire rod for forming the skeleton portion 111 include known metals or metal alloys typified by a stainless steel, an Ni—Ti alloy (Nitinol), a titanium alloy, and the like. Also, an X-ray detectable alloy material may be used. In this case, a position of the bile duct stent 100 can be confirmed from outside of the body. Incidentally, the skeleton portion 111 may be made of a material other than metal materials (e.g. ceramic, resin, or the like).

Additionally, in the skeleton portion 111, there is a difference in a winding frequency per a unit length of the metal wire rod in the axial direction between the first and second end portion 110a and 110b sides and a middle side. The middle side portion of the stent main body section 110 in the axial direction exerts a relatively large expanding force, and the first and second end portion 110a and 110b sides of the stent main body section 110 in the axial direction exert a relatively small expanding force.

That means, the bile duct stent 100 is placed such that the middle side portion in the axial direction of the stent main body section 110 corresponds to a predetermined position of the bile duct B (e.g. a central or similar position of an occluded site or stenosis site). A region R1 (hereinafter referred to as a proximal side region R1) on the first end portion 110a side where the removal assistant 130 is provided, and a region R2 (hereafter referred to as a distal side region R2) on the second end portion 110b side exert expanding forces that are smaller than an expanding force exerted by a region R3 (hereinafter referred to as a middle side region R3) on the middle side. Herein, the compared expanding forces are values when inner diameters of the proximal side region R1, the distal side region R2, and the middle side region R3 are equal, typically when the bile duct stent 100 is placed in the bile duct B. Since the expanding force depends on a ratio of the skeleton portion 111 (amount of the skeleton), a magnitude of the expanding force can be determined depending on a density of the skeleton portion 111. That means, in the proximal side region R1 and the distal side region R2 of the stent main body section 110, the skeleton portion 111 is "sparser" than the middle side region R3.

Specifically, when the skeleton portion 111 is formed by weaving one wire rod with a substantially constant wire diameter (sectional area) while spirally winding the wire rod, the portion having a smaller winding frequency per the unit length in the axial direction (portion having a long spiral pitch) is "sparser" than the portion having a larger winding frequency (portion having a short spiral pitch) in the skeleton portion 111. That means, the proximal side region R1 and the distal side region R2 of the stent main body section 110 has a relatively smaller winding frequency per the unit length in the axial direction than of the middle side region R3.

For example, when the bile duct stent 100 in the most expanded state has a straight cylindrical shape, since the inner diameter of the bile duct stent 100 is constant over the whole length in the axial direction, the magnitude of the expanding force can be determined depending on the density of the skeleton portion 111 regardless of the expansion state. Thus, in the stent main body section 110, the expanding force exerted by the middle side region R3 corresponding to the predetermined position of the occluded site or the stenosis site of the bile duct B is relatively large, so that adhesiveness to the occluded site or the stenosis site of the bile duct B can be improved, and the stent is hardly displaced.

In addition, since the proximal side region R1 and the distal side region R2 exert relatively small expanding forces, an axial force of the stent main body section 110 can be prevented from increasing excessively. That means, since the stent main body section 110 can follow a shape of the bile duct B even if the middle side region R3 exerts a large expanding force, it is possible to prevent development of so-called kink in which the end portion of the stent main body section 110 is embedded in the bile duct wall with time and occluded by the axial force.

Herein, when the bile duct stent 100 is removed, the proximal side region R1 of the stent main body section 110 is a portion closest to a recovery catheter 22. In the indwelling state, the proximal side region R1 of the stent main body section 110 exerts an expanding force smaller than the expanding force exerted by the middle side region R3, and adhesiveness of the proximal side region R1 to the bile duct wall is lower than of the middle side region R3. Thereby, the proximal side region R1 of the stent main body section 110 is easily peeled from the bile duct wall, so that workability for removing and recovering the bile duct stent 100 is improved.

In addition, when the bile duct stent 100 is placed, the distal side region R2 of the stent main body section 110 is a portion that is first released from a sheath. That means, when the stent is accommodated in the sheath, the distal side region R2 of the stent main body section 110 exerts an expanding force smaller than the expanding force exerted by the middle side region R3, and adhesiveness of the distal side region R2 to the sheath is lower than of the middle side region R3. Thereby, when the bile duct stent 100 is released by relatively moving the sheath and the bile duct stent 100, a friction resistance between the distal side region R2 of the stent main body section 110 and the sheath is reduced, so that the bile duct stent 100 can be easily released.

Incidentally, a material, a wire type (e.g. a round wire rod such as a wire, or a rectangular wire rod obtained by laser cutting), a wire diameter (sectional area), a folding frequency and a folded shape in the circumferential direction (a number and a shape of the crest portions), an interval in the axial direction between the wire rods (spiral pitch (amount of skeleton per a unit length)), and the like, of the wire rod for forming the skeleton portion 111 are appropriately selected on the basis of flexibility of the stent main body section 110 required depending on the living body lumen where the stent is placed. Herein, the flexibility refers to bendability of the stent main body section 110, and is defined particularly depending on a bending rigidity in the axial direction. That means, the high flexibility of the stent main body section 110 means a property that the stent has a moderately low bending rigidity in the axial direction and can follow the shape of the living body lumen or the sheath without causing kink in the living body lumen or the sheath.

The membrane portion 112 is a membrane body for forming the flow path for bile, and is disposed so as to cover the peripheral face of the skeleton portion 111. The membrane portion 112 may be disposed on the outer peripheral face and the inner peripheral face of the skeleton portion 111 so as to sandwich the skeleton portion 111, or disposed only on the outer peripheral face or only on the inner peripheral face of the skeleton portion 111.

Examples of the material for forming the membrane portion 112 include a silicon resin, a fluorine resin such as PTFE (polytetrafluoroethylene), a polyester resin such as polyethylene terephthalate, and the like.

The stretch restriction portion 113 is disposed, for example, along the axial direction of the skeleton portion 111 and is formed from a rectangular long member. Specifically, the stretch restriction portion 113 is fixed to the outer peripheral face (inside of the membrane portion 112) of the skeleton portion 111 (by adhesion, for example) so as to extend to both end portions in the axial direction of the skeleton portion 111.

In addition, for example, the stretch restriction portion 113 is made of a biocompatible thread (e.g. polyester thread, or the like) or cloth (woven fabric (textile) or knit) and has a strength capable of restricting stretch of the skeleton portion 111 in the axial direction at least without impairing expandability of the bile duct stent 100 in the radial direction. In addition, a plurality of the stretch restriction portions 113 may be disposed at a predetermined interval in the circumferential direction. For example, two stretch restriction portions 113 are arranged at different positions 180 degrees away from each other.

When the bile duct stent 100 is contracted in the radial direction and accommodated in the sheath, the stretch restriction portion 113 suppresses the stretch in the axial direction. Thus, when the bile duct stent 100 is accommodated in the sheath, compared to a stent having no stretch restriction portion 113, a length in the axial direction of the bile duct stent 100 is shorter, a contact area between the bile duct stent 100 and the sheath is smaller, and the friction resistance when releasing the bile duct stent 100 from the sheath is lower. In addition, when the bile duct stent 100 is released from the sheath and the stent main body section 110 expands, a reduction rate in the axial direction decreases, so that the bile duct stent 100 can be placed on a target indwelling site in the bile duct B.

The valve section 120 is disposed on the first end portion 110a of the stent main body section 110. That means, the valve section 120 is disposed on a downstream side end portion 110a of the stent main body section 110, positioned on a downstream side in the flow direction of a fluid (bile) flowing in the bile duct B. The valve section 120 is formed from a membrane body similarly to the membrane portion 112 of the stent main body section 110, and is formed integrally with the membrane portion 112.

The valve section 120 has a streamer shape whose outer shape deforms by a fluid pressure. The valve section 120 has a bile (fluid) inlet 120a on the stent main body section 110 side, and a bile outlet 120b on the opposite side to the stent main body section 110. The outlet 120b has a flat shape in which a width in a first direction D1 orthogonal to the axial direction is smaller than a width in a second direction D2 substantially orthogonal to the axial direction and the first direction D1.

The outlet 120b through which bile does not passes is occluded in a straight line. On the other hand, the outlet 120b through which bile passes is widened by an internal pressure due to bile. Thereby, bile can be prevented from reversely flowing into the bile duct stent 100 without inhibiting the flow of bile. Incidentally, a shape of the outlet 120b through which bile passes is not particularly limited as long as bile can pass, and examples of the shape include an elliptical shape, a long rectangular shape, and the like.

In addition, the valve section 120 has a tapered portion 121 and a flat portion 122. The tapered portion 121 is consecutively connected to the membrane portion 112 of the stent main body section 110. One end of the tapered portion 121 is the inlet 120a. The tapered portion 121 is formed such that a width in the second direction D2 scarcely changes but a width in the first direction D1 decreases from the inlet 120a toward the flat portion 122. The flat portion 122 is consecutively connected to the tapered portion 121. One end of the flat portion 122 is the outlet 120b. The flat portion 122 is formed such that the widths in the first direction D1 and the second direction D2 are maintained. That means, the valve section 120 is composed of a film-like check valve. This check valve makes it possible to more effectively prevent bile from flowing reversely.

Furthermore, the membrane body of the valve section 120 is formed along two support portions 123 and 124. Specifically, the support portions 123 and 124 are formed integrally with the skeleton portion 111. For example, on a frontmost portion positioned on the valve section 120 side of the skeleton portion 111, two crest portions opposite to each other in the radial direction are higher than the other crest portions, and the two crest portions protruding toward the distal side functionally serves as the support portions 123 and 124. That means, the support portions 123 and 124 have a V-shape that is closed on the distal side and opened on the rear end.

In addition, in the support portions 123 and 124, for example, V-shaped apex portions 123a and 124a are positioned on the distal side of the tapered portion 121, and two foot portions 123b and 124b are positioned on the inlet 120a side of the tapered portion 121 (side consecutively connected to the stent main body section 110).

Also, the two support portions 123 and 124 are arranged opposite to each other in the second direction D2 e.g. at an 180° interval in the circumferential direction.

Incidentally, the support portions 123 and 124 may be biased such that, for example, the apex portions 123a and 124a are separated from each other along the second direction D2. As a result, when bile does not pass through the outlet 120b, the distal end side of the tapered portion 121 (rear end side of the flat portion 122) is pulled toward both outsides in the second direction D2 by the two support portions 123 and 124, and therefore the outlet 120b of the valve section 120 can be easily closed. Thus, when bile does not flow, the valve section 120 can quickly transition from the open state to the closed state, so that bile can be more effectively prevented from flowing reversely.

The removal assistant 130 is an auxiliary implement used for removing the bile duct stent 100 placed in the bile duct B. The removal assistant 130 has an engaging portion 130a with which a hooking implement (snare: (recovery member) 22a (see FIG. 4A) is engaged disposed on the distal end of the recovery catheter. This engaging portion 130a may be formed, for example by bending a wire rod and may have a shape such as a hook shape, or a loop shape.

In addition, the removal assistant 130 extends in the axial direction from the stent main body section 110 (e.g. end portion of the skeleton portion 111), and the engaging portion 130a is disposed on the distal end of the removal assistant 130. That means, the removal assistant 130 is disposed so as to protrude in the axial direction from the first end portion 110a (downstream side end portion) among both end portions in the axial direction of the stent main body section 110.

Incidentally, for the wire rod for forming the removal assistant 130, for example, the same wire rod as for the skeleton portion 111 can be applied, and the removal assistant 130 may be formed integrally with the skeleton portion 111.

FIG. 4A to FIG. 4D are diagrams illustrating state transition when recovering the bile duct stent 100 placed in the bile duct B. Incidentally, FIG. 4A to 4D schematically illustrate the bile duct stent 100.

Figure 4A:
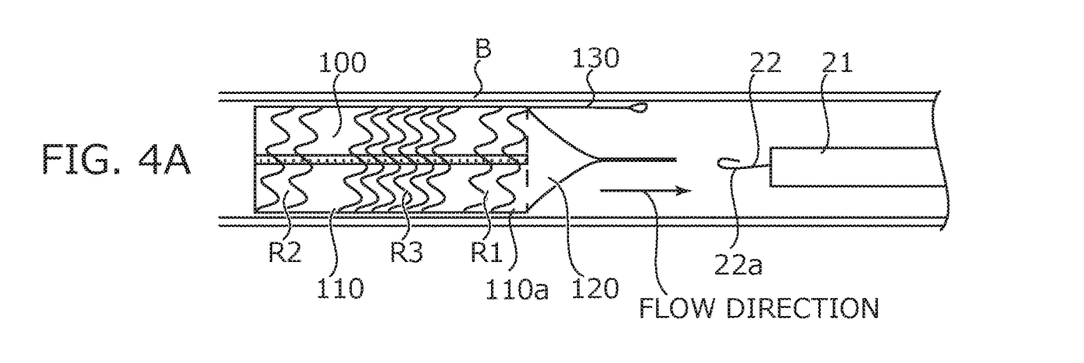
FIG. 4A is a diagram illustrating a state of state transition in a process for recovering the bile duct stent placed in a bile duct.

As illustrated in FIG. 4A, the bile duct stent 100 is placed such that the first end portion 110a is positioned on the downstream side of the bile flow direction. In this state, the recovery catheter 22 is introduced from the downstream side of the flow direction.

Figure 4B:
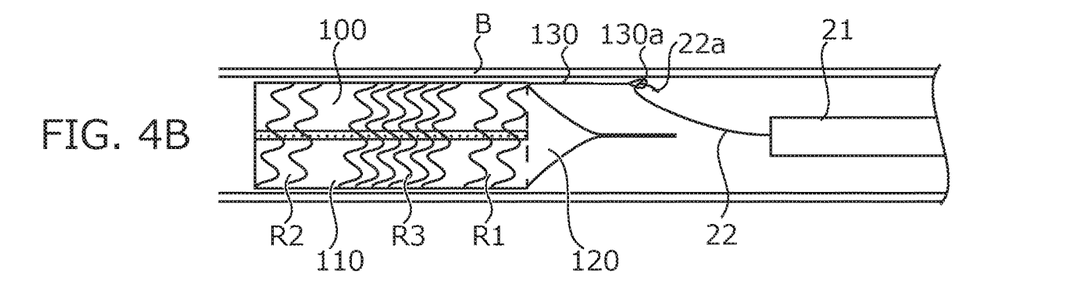
FIG. 4B is a diagram illustrating a state of state transition in the process for recovering the bile duct stent placed in the bile duct.
Figure 4C:
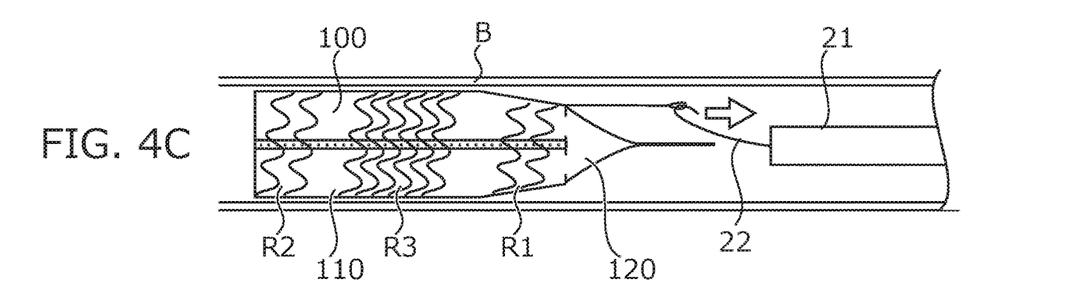
FIG. 4C is a diagram illustrating a state of state transition in the process for recovering the bile duct stent placed in the bile duct.

The hooking implement 22a of the recovery catheter 22 is hooked on the engaging portion 130a of the removal assistant 130 and the recovery catheter 22 is pulled, the proximal side region R1 of the stent main body section 110 stretches in the axial direction and contracts inward in the radial direction (see FIG. 4B and FIG. 4C). Thereby, the proximal side region R1 of the stent main body section 110 is peeled off from the bile duct wall to which the proximal side region R1 has adhered.

Figure 4D:
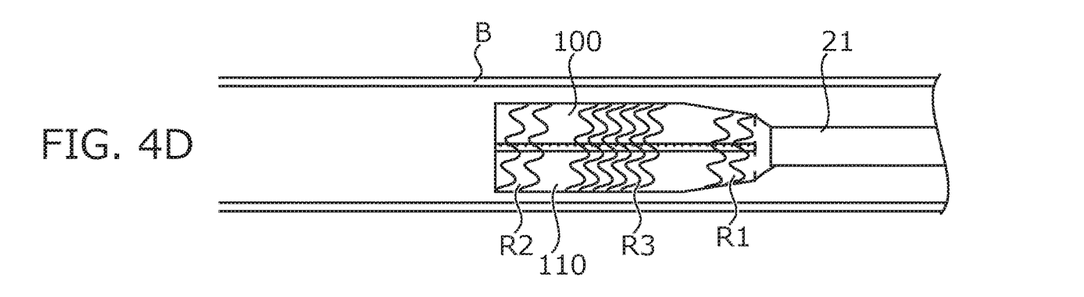
FIG. 4D is a diagram illustrating a state of state transition in the process for recovering the bile duct stent placed in the bile duct.

Then, the recovery catheter 22 is pulled and the bile duct stent 100 is drawn into a recovery sheath 21, so that the bile duct stent 100 is removed and recovered (see FIG. 4D). In an initial stage of the removal operation, the proximal side region R1 of the stent main body section 110 is first peeled off from the bile duct wall, and therefore the middle side region R3 and the distal side region R2 positioned on the upstream side can also be easily peeled off from the bile duct wall.

In this way, the bile duct stent 100 according to this embodiment is placed in the bile duct B (living body lumen) and has the stent main body section 110 in a cylindrical shape. The stent main body section 110 is formed expandably and contractibly in the radial direction substantially orthogonal to the axial direction, in which one portion (middle side region R3) corresponding to a predetermined position (e.g. the central position of the occluded site or stenosis site) on the indwelling site in the bile duct B exerts relatively large expanding forces, and the different portions (proximal side region R1, distal side region R2) that are different in axial position from that of the aforementioned one portion, exert relatively small expanding forces.

According to the bile duct stent 100, since the one portion (middle side region R3) corresponding to a predetermined position on the indwelling site in the bile duct B exerts a relatively large expanding force in the stent main body section 110, adhesiveness to, for example, the occluded site or stenosis site in the bile duct tube B can be improved, and the stent can be made difficult to displace from the indwelling site. Furthermore, in the stent main body section 110, the different portions (proximal side region R1, distal side region R2) positioned on the end portion sides in the axial direction of the aforementioned one portion exert relatively small expanding forces, so that flexibility can be increased and followability to the bile duct B can be improved.

In this way, the bile duct stent 100 can be made difficult to displace from the indwelling site in the bile duct B, and followability of the bile duct stent 100 to the bile duct B can be improved. In addition, development of kink by the axial force of the stent main body section 110 with time can be prevented.

In addition, the bile duct stent 100 further includes the removal assistant 130 provided on one (first end portion 110a) of the both end portions in the axial direction of the stent main body section 110 and for assisting removal of the stent main body section 110 from the bile duct B (living body lumen). The bile duct stent 100 is configured such that when the removal assistant 130 is pulled in the axial direction, the stent main body section 110 contracts inward in the radial direction while stretching in the axial direction on the first end portion 110a side.

Thereby, when the bile duct stent 100 is pulled in the axial direction via the removal assistant 130 provided on the first end portion 110a having the expanding force relatively smaller than of the middle portion side, the stent main body section 110 stretches in the axial direction and contracts inward in the radial direction, so that the stent can be easily peeled off from the bile duct wall. Thus, workability for removing the placed bile duct stent 100 can be improved.

Additionally, in the bile duct stent 100, the first end portion 110a refers to the downstream side end portion positioned on the downstream side of the flow direction of bile (fluid) flowing in the bile duct B (living body lumen). The bile duct stent 100 is removed by introducing the recovery catheter from the downstream side end portion. Thereby, the removal direction of the bile duct stent 100 coincides with the flow direction of bile, so that the bile duct stent 100 can be easily removed without receiving a fluid resistance.

In addition, the bile duct stent 100 is formed from a membrane body and includes the valve section 120 disposed on the downstream side end portion of the stent main body section 110, positioned on the downstream side in the flow direction of bile (fluid) flowing in the bile duct B (living body lumen). The valve section 120 has the outlet 120b from which bile flows out. The outlet 120b has a width in the first direction D1 orthogonal to the axial direction, that is smaller than a width in the second direction D2 substantially orthogonal to the axial direction and the first direction. This makes it possible to prevent bile from reversely flowing into the bile duct stent 100.

As described above, the invention made by the present inventors has been specifically explained on the basis of the embodiments, but the present invention is not limited to the above embodiments, and can be modified without departing from the gist of the present invention.

For example, in the above embodiment, one portion of the stent main body section 110 corresponding to the predetermined position (e.g. the central position of the occluded site or stenosis site, or the like) on the indwelling site in the bile duct B is set as an middle side portion (middle side region R3) in the axial direction of the stent main body section 110, and different portions on the axial-direction end portion sides of the aforementioned one portion are set as the both end side portions in the axial direction (proximal side region R1 and distal side region R2) of the stent main body section 110, but this configuration is merely an example and the present invention is not limited to this configuration. That means, any configuration is allowed as long as the portion corresponding to the predetermined position on the indwelling site in the bile duct B exerts a relatively large expanding force. For example, the expanding force of the distal side region R2 of the stent main body section 110 may be increased, the distal side region R2 may be disposed corresponding to the predetermined position on the indwelling site in the bile duct B, and the expanding force of the proximal side portion of the distal side region R2 may be decreased. Alternatively, the expanding force of the distal side region R2 of the stent main body section 110 may be decreased, and the expanding forces of the middle side region R3 and the proximal side region R1 of the stent main body section 110 may be increased. Alternatively, portions with a large expanding force and portions with a small expanding force may be arranged alternately in the axial direction.

Incidentally, no matter what the aforementioned configuration is, whether or not at least one removal assistant 130 is provided can be appropriately and arbitrarily changed.

In addition, in this embodiment, the expanding force is controlled by adjusting a winding frequency per a unit length of the metal wire rod for forming the skeleton portion 111, but the expanding force may be controlled by other methods. For example, the expanding force can be controlled by appropriately selecting a wire diameter, a circumferential folding frequency, a folding shape, and the like, of the metal wire rod for forming the skeleton portion 111.

In addition, the skeleton portion 111 may be a laser-cut type formed by laser-cutting a metal cylindrical member. Also in this case, the expanding force can be controlled by appropriately selecting a material, a wall thickness, a shape after laser cutting, an interval between skeletons, and the like, of the cylindrical member on the basis of flexibility of the stent main body section 110 required depending on the living body lumen where the stent is placed. Furthermore, in this embodiment, the expanding force on the second end portion 110b side as the upstream side in the fluid flow direction is also smaller than the expanding force on the middle portion side, but the expanding force on the second end portion 110b side may be equivalent to the expanding force on the middle portion side.

Additionally, in this embodiment, although the bile duct stent 100 including the valve section 120 has been explained, the present invention can also be applied to a stent having no valve section, i.e. composed only of a stent main body section. In addition, the stent main body section may be composed of a bare stent consisting only of skeleton portions.

In addition, for example, in this embodiment, although the case where the valve section 120 has the flat portion 122 has been explained, the valve section 120 does not necessarily have the flat portion 122. However, as in this embodiment, the valve function is improved rather by installing the flat portion 122 on the valve section 120. Also, the valve section 120 does not necessarily have the support portions 123 and 124. For example, the membrane body is formed along the substrate having the same shape as of the valve section 120, so that the shape of the valve section 120 can be maintained without the support portions 123 and 124.

Furthermore, in this embodiment, although the case where the stent main body section 110 has two stretch restriction portions 113 has been explained, the stretch restriction portions 113 may be omitted, alternatively three or more stretch restriction portions 113 may be disposed at a predetermined interval in the circumferential direction, alternatively the stretch restriction portions 113 may be disposed over the whole peripheral face of the stent main body section 110 (inner peripheral face or outer peripheral face of the skeleton portion 111).

In addition, the stretch restriction portions 113 may be disposed outside the membrane portion 112. In this case, when the bile duct stent 100 is placed in the bile duct B, the bile duct wall and the stretch restriction portions 113 come into contact with each other, and therefore the bile duct wall make inroads into the stretch restriction portions 113. Thus, the bile duct stent 100 can be prevented from being displaced from the indwelling position. That means, the stretch restriction portions 113 can functionally serves as a displacement-preventing means for the bile duct stent 100.

In addition, the stent main body section 110 may or may not have a straight cylindrical shape as described in this embodiment, and may have, for example, a spindle shape in the most expanded state. In this case, even if density of the skeleton portion 111 is constant over the whole length in the expanded state, the middle side region R3 is "denser" when the stent is placed in the bile duct B (the inner diameter is constant), and therefore the proximal side region R1 and the distal side region R2 exert expanding forces smaller than the expanding force exerted by the middle side area R3.

Furthermore, the present invention can be applied not only to the bile duct stent 100 explained in this embodiment but also to a stent that is placed in a living body lumen such as digestive system lumen and blood vessel. In this case, the fluid that flows through the living body lumen includes e.g. food immediately after intake, that has not been digested at all, decomposed food that has passed through the digestive tract, a matter that has not been digested even through the digestive tract (e.g. stool, or the like), and the like, regardless of a state of the matter.

In addition, although the case where the stent main body section 110 has a straight cylindrical shape has been described, this case is merely an example and the present invention is not limited to this case. The stent main body section 110 may have a curved shape depending on the indwelling site, or the stent main body section 110 will have a curved shape following a bile duct shape after placement.

Furthermore, in this embodiment, although the configuration in which the removal assistant 130 is provided on the first end portion 110a (downstream side end portion) positioned on the downstream side in the flow direction of bile (fluid) in the stent main body section 110 has been described as an example, this configuration is merely an example, and the present invention is not limited to this configuration. For example, the removal assistant 130 may be provided on the second end portion 110b (upstream side end portion) positioned on the upstream side in the flow direction of bile (fluid) in the stent main body section 110. In addition, a plurality of the removal assistants 130 may be provided on at least one end side in the axial direction of the stent main body section 110. That means, the number of the removal assistants 130 is not limited to one, and a plurality of the removal assistants 130 may be provided.

In addition, the following inventions are also disclosed in this embodiment.

This means, a stent that is placed in the bile duct B (living body lumen), includes the tent main body section 110 in a cylindrical shape, the removal assistant 130 that is provided on the first end portion 110a (downstream side end portion) positioned on the downstream side in the flow direction of bile (fluid) flowing in the bile duct B among both end portions in the axial direction of the stent main body section 110 and assists removal of the stent main body section 110 from the bile duct B, and the valve section 120 that is formed from a membrane body and consecutively connected to the first end portion 110a of the stent main body section 110. The stent main body section 110 is formed expandably and contractibly in the radial direction substantially orthogonal to the axial direction. The valve section 120 has the outlet 120b from which bile flows out. The outlet 120b has a width in the first direction D1 orthogonal to the axial direction that is smaller than the width in the second direction D2 substantially orthogonal to the axial direction and the first direction D1. Constitutionally, when the removal assistant 130 is pulled in the axial direction, the stent main body section 110 contracts inward in the radial direction while stretching in the axial direction on the first end portion 110a side.

In addition, a stent that is placed in the bile duct B (living body lumen), includes the stent main body section 110 in a cylindrical shape, and the valve section 120 that is formed from a membrane body and disposed on the first end portion 110a (downstream side end portion) positioned on the downstream side in the flow direction of the fluid flowing in the bile duct B among both end portions in the axial direction of the stent main body section 110. The stent main body section 110 is formed expandably and contractibly in the radial direction substantially orthogonal to the axial direction, in which the first end portion 110a side exerts a relatively smaller expanding force than an expanding force exerted by the middle portion side. The valve section 120 has the outlet 120b from which bile flows out. The outlet 120b has a width in the first direction D1 orthogonal to the axial direction that is smaller than the width in the second direction D2 substantially orthogonal to the axial direction and the first direction D1. Constitutionally, when the first end portion 110a of the stent main body section 110 is pulled in the axial direction, the first end portion 110a side of the stent main body section 110 stretches in the axial direction and contracts inward in the radial direction.

The embodiments disclosed in this specification should be regarded as examples in all regards and considered to be unrestrictive. The scope of the present invention is stipulated not by the aforementioned explanation but by claims, and intended to include meanings equivalent to claims and all changes within the scope of claims.

Disclosure contents of specifications, figures, and abstracts included in Japanese Patent Application No. 2018-086854 filed on Apr. 27, 2018 are all incorporated in this application.

DESCRIPTION OF REFERENCE NUMERALS

100 Bile duct stent (Stent)
110 Stent main body section
110a First end portion
110b Second end portion
111 Skeleton portion
112 Membrane portion
113 Stretch restriction portion
120 Valve section
121 Tapered portion
122 Flat portion
123, 124 Support portion
130 Removal assistant

What is claimed is:

1. A stent that is placed in a living body lumen, the stent comprising:
a stent main body section including a skeleton portion formed into a cylindrical shape by spirally winding a wire rod; and
a valve section provided in a downstream end portion of the stent main body section that is located downstream in a flow direction of a fluid flowing in the living body lumen, wherein
the stent main body section is formed expandably and contractibly in a radial direction substantially orthogonal to an axial direction, and has a portion that corresponds to a predetermined position on an indwelling site in the living body lumen, the portion exerts a larger expanding force than at least one of two end portions that is different in axial position from the portion,
the skeleton portion is bent in such a way that crest portions and trough portions are alternately formed in the axial direction, and includes a downstream skeleton portion located at the most downstream end of the skeleton portion,
the crest portions of the downstream skeleton portion include two crest portions and other crest portions,
the two crest portions face and separate each other in a first direction orthogonal to the axial direction,
the other crest portions are disposed between the two crest portions in a circumferential direction,
the two crest portions protrude more downstream in the flow direction than the other crest portions,
the valve section has a membrane body forming an inlet and an outlet through which the fluid flows and two support portions supporting the membrane body, and has a tapered shape in which a width in a second direction orthogonal to the first direction in the axial cross section gradually decreases toward a downstream of the flow direction, and
the two support portions are each formed in a V-shape by the two crest portions and apply force to the outlet to separate the two crest portions from each other along the first direction.

2. The stent according to claim 1, further comprising a removal assistant that assists in removal of the stent main body section from the living body lumen, wherein
the removal assistant is provided in a bent portion between the two crest portions of the downstream skeleton portion,
when the removal assistant is pulled in the axial direction, the skeleton portion is deformed and the downstream end portion of the stent main body section contracts inward in the radial direction while stretching in the axial direction.

3. The stent according to claim 2, wherein the removal assistant includes an engaging portion with which a recovery member for recovering the stent from the living body lumen is engaged, the engaging portion being formed by bending a wire rod.

4. The stent according to claim 1, further comprising a stretch restriction portion configured to suppress stretching of the stent main body section in the axial direction, wherein
the stretch restriction portion is disposed along the axial direction on the stent main body section, and a downstream end portion thereof is located at an inlet side of at least one of the two support portions.

* * * * *